(12) United States Patent
Dzyubak et al.

(10) Patent No.: US 10,132,905 B2
(45) Date of Patent: Nov. 20, 2018

(54) SYSTEMS AND METHODS FOR A MAGNETIC RESONANCE ELASTOGRAPHY PHANTOM

(71) Applicant: MAYO FOUNDATION FOR MEDICAL EDUCATION AND RESEARCH, Rochester, MN (US)

(72) Inventors: Bogdan Dzyubak, Rochester, MN (US); Jun Chen, Rochester, MN (US); Richard Ehman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 137 days.

(21) Appl. No.: 15/399,479

(22) Filed: Jan. 5, 2017

(65) Prior Publication Data

US 2017/0192077 A1 Jul. 6, 2017

Related U.S. Application Data

(60) Provisional application No. 62/274,860, filed on Jan. 5, 2016.

(51) Int. Cl.
*G01V 3/00* (2006.01)
*G01R 33/58* (2006.01)
*A61B 5/055* (2006.01)

(52) U.S. Cl.
CPC .............. *G01R 33/58* (2013.01); *A61B 5/055* (2013.01)

(58) Field of Classification Search
USPC ......................................................... 324/318
See application file for complete search history.

(56) References Cited

U.S. PATENT DOCUMENTS

| | | | | |
|---|---|---|---|---|
| 5,592,085 | A * | 1/1997 | Ehman .................... | A61B 5/055 324/307 |
| 7,034,534 | B2 * | 4/2006 | Ehman .............. | G01R 33/56358 324/318 |
| 7,307,423 | B2 * | 12/2007 | Ehman .............. | G01R 33/56358 324/318 |
| 7,462,488 | B2 * | 12/2008 | Madsen ................. | A61B 5/055 422/536 |
| 2010/0167251 | A1 * | 7/2010 | Boutchko .............. | A61B 5/416 434/267 |
| 2018/0098752 | A1 * | 4/2018 | Rouze .................... | A61B 8/485 |

* cited by examiner

*Primary Examiner* — Rodney Fuller
(74) *Attorney, Agent, or Firm* — Quarles & Brady LLP

(57) ABSTRACT

A phantom for magnetic resonance elastography (MRE) is provided. In particular, systems and methods for a phantom that is capable of generating a wave-like pattern in MRE images where a wavelength of the generated wave-like pattern is controlled by the phantom geometry. The geometrically controlled wavelength enables the phantom to calibrate MRE image acquisition and mechanical property calculation.

20 Claims, 5 Drawing Sheets

SYSTEMS AND METHODS FOR A MAGNETIC RESONANCE ELASTOGRAPHY PHANTOM

CROSS-REFERENCES TO RELATED APPLICATIONS

This application is based on, claims priority to, and incorporates herein by reference in its entirety, U.S. Provisional Application Ser. No. 62/274,860, filed Jan. 5, 2016, and entitled, "Systems and Methods for a Magnetic Resonance Elastography Phantom."

STATEMENT REGARDING FEDERALLY SPONSORED RESEARCH

This invention was made with government support under EB001981 awarded by the National Institutes of Health. The government has certain rights in the invention.

BACKGROUND

The disclosure relates generally to magnetic resonance elastography (MRE) and, more specifically, to a phantom for MRE quality assurance.

MRE is gaining wider clinical applicability due to its ability to noninvasively and quantitatively measure tissue stiffness. MRE is a multi-step process beginning with the induction of shear waves into the tissue to be examined via an external source of vibration. The shear waves are then imaged with a phase-contrast MRI pulse sequence with motion-encoding gradients synchronized with the applied vibration. The resulting wave images of the wave motion are inverted to produce an elastogram image and calculate a mechanical property of the tissue.

MRE is analogous to manual palpation, which has a long history in the practice of medicine as a clinical diagnostic tool for examining tissues such as the breast and thyroid for focal and diffuse diseases. In fact, MRE of the liver has already matured to a point where it is replacing needle biopsies for the diagnosis of fibrosis and cirrhosis in a growing number of clinical practices.

To assure accurate calculations of the mechanical properties, routine calibrations are required. As generally described above, MRE utilizes the oscillating stress produced by the shear waves that propagate through the organ, or tissues to be imaged, to elicit information about the tissue. Thus, to perform calibrations, specialized phantoms have been created that are formed of particular materials that are both MR-visible and have known stiffness/elasticity. Unfortunately, the properties, including the stiffness/elasticity of these materials change over time and can vary due to fine differences in the manufacturing process. Thus, these specialized MR-visible elastography phantoms must be regularly replaced and it is challenging to ensure that phantoms used for calibration at different sites have matched properties.

Thus, it would be desirable to have calibration and quality control systems and methods for MRE that do not rely on the variable properties of a specialized material.

BRIEF SUMMARY

The present disclosure provides systems and methods for a phantom that is capable of generating a wave-like pattern in MRE images where a wavelength of the generated wave-like pattern is controlled by the phantom geometry and without relying on mechanical properties of specialized materials that change over time. For example, the phantom is designed to generate these wave-like patterns with materials, such as water or an MRI-visible gel with broadly compatible properties. The geometrically controlled wavelength enables the phantom to calibrate MRE image acquisition and mechanical property calculation.

In one aspect, the present disclosure provides a phantom for a magnetic resonance elastography (MRE) system. The phantom includes an MRI visible structure configured to be flexible when subjected to displacing forces, a first plurality of supports each engaging one side of the MRI visible structure and spaced apart such that adjacent pairs of the first plurality of supports define a first distance therebetween, and a second plurality of supports each engaging another opposing side of the MRI visible structure and spaced apart such that adjacent pairs of the second plurality of supports define the first distance therebetween, Repeated motion of the second plurality of moveable supports in a displacement direction causes displacement of the MRI visible structure to create a wave-like pattern in the MRI visible structure.

In another aspect, the present disclosure provides a method for calibrating a magnetic resonance imaging (MRI) system used to acquire magnetic resonance elastography (MRE) data with a phantom. The phantom includes an MRI visible structure. The method includes engaging the phantom with an MRE driver configured to impart an oscillating motion to the phantom by displacing flexible portions of the phantom to create alternating areas of high phase and low phase forming a wave-like pattern defining a wavelength geometrically controlled by the phantom. The method further includes acquiring with the MRI system, an MRE data from the phantom while using the MRE driver to create the alternating areas of high phase and low phase in a wave-like pattern, and analyzing the one MRE data to determine a calibration state of the MRI system.

In yet another aspect, the present disclosure provides a phantom for a magnetic resonance elastography (MRE) system. The phantom includes an MRI visible structure forming an elongated, flexible body, a first plurality of supports each engaging one side of the MRI visible structure and spaced apart such that adjacent pairs of the first plurality of supports define a first distance therebetween, and a second plurality of supports each engaging another opposing side of the MRI visible structure and spaced apart such that adjacent pairs of the second plurality of supports define the first distance therebetween. The phantom further includes a driver configured to repeatedly move the second plurality of supports to cause displacement of the MRI visible structure to create a wave-like pattern in the MRI visible structure.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

Currently, mechanical property calculation calibrations for magnetic resonance elastography (MRE) are performed using a gel-based phantom manufactured by varying concentrations of a fixative in an attempt to obtain tissue-like mechanical properties. However, the actual, or exact, mechanical properties of the gel-based phantom are unknown and must be approximated by calculation based on a pre-determined relationship between the mechanical properties and fixative concentration. Additional factors, such as heat regime during manufacturing, can affect the gel-based phantom's mechanical properties. Further, the gel-based phantom's physical properties change over time, which requires newly manufactured gel-based phantoms to be aged for a period of time (e.g., up to 3 months) before use, and old gel-based phantoms to be discarded due to inaccuracies after a prolonged use (e.g., approximately 12 months). The difficulty in controlling, or knowing, the exact mechanical properties of current gel-based phantoms combined with the need to periodically replace old gel-based phantoms, pose a complex challenge for long-term MRE studies.

Due to the current difficulties in performing mechanical property calculation calibrations for MRE, it would be desirable to have a phantom that is capable of generating a wave-like pattern in MRE images where the wavelength is controlled by the phantom geometry. Geometrically controlling the wavelength generated by the phantom enables the phantom to generate a fixed, known, wavelength and, therefore, the phantom would not be subject to inaccuracies due to unknown mechanical properties. Further, the phantom may be tunable (i.e., configured to generate different, geometrically controlled, wavelengths) by varying the phantom geometry.

Figure 1:
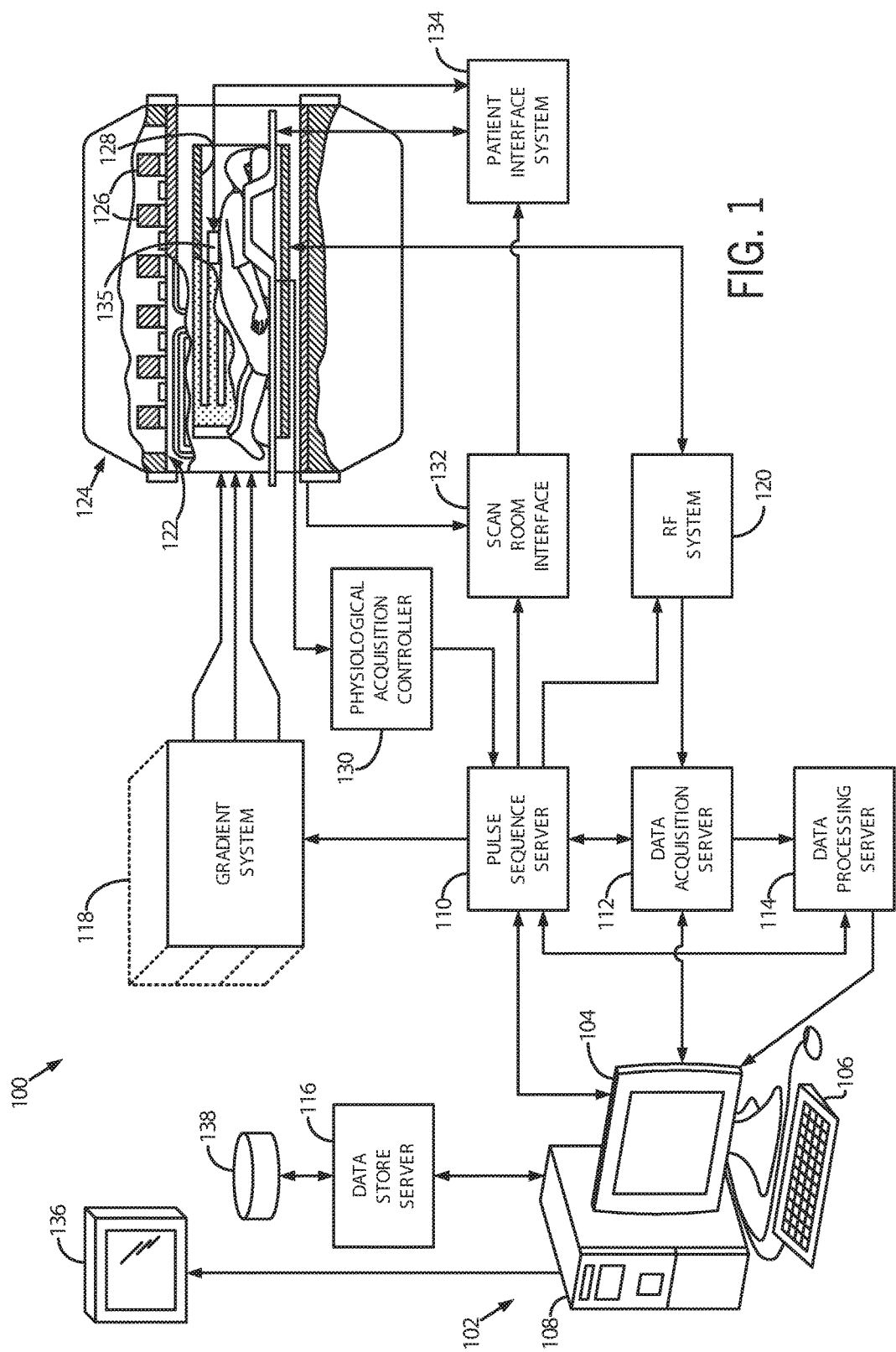
FIG. 1 shows a magnetic resonance imaging (MRI) system according to one aspect of the present disclosure.

The present disclosure provides systems and methods for a phantom to calibrate MRE mechanical property calculations. Referring to FIG. 1, an exemplary magnetic resonance imaging ("MRI") system 100 for use with the present disclosure is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 may be separate and distinct from the hardware of an MRI or other imaging system. Whether specifically configured with the imaging system or communicating with the imaging system, the workstation 102 is able to communicate with at least some of a pulse sequence server 110, a data acquisition server 112, a data processing server 114, and a data store server 116 to access information available from the imaging system and/or control the imaging system. That is, the workstation 102 and the server 110, 112, 114 and 116 are able to communicate.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad (1);$$

and the phase of the received MR signal may also be determined:

$$\phi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient interface system 134 is accessed to move the patient to desired positions during the scan or control operation of an MRE driver 135, such as will be described.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 re conveyed back to the workstation 102 for access by an operator. Real-time images are stored in a data base memory cache (not shown in FIG. 1), from which they may be output to operator display 104 or a display 136 that is located near the magnet assembly 124 for use by attending physicians. Also, images are stored in a host database on disc storage 138. When such images have been reconstructed and transferred to storage 138, the data processing server 114 notifies the data store server 116 or the workstation 102. The workstation 102 may be used by an operator to archive the images, or send the images via a network to other facilities.

Figure 2:
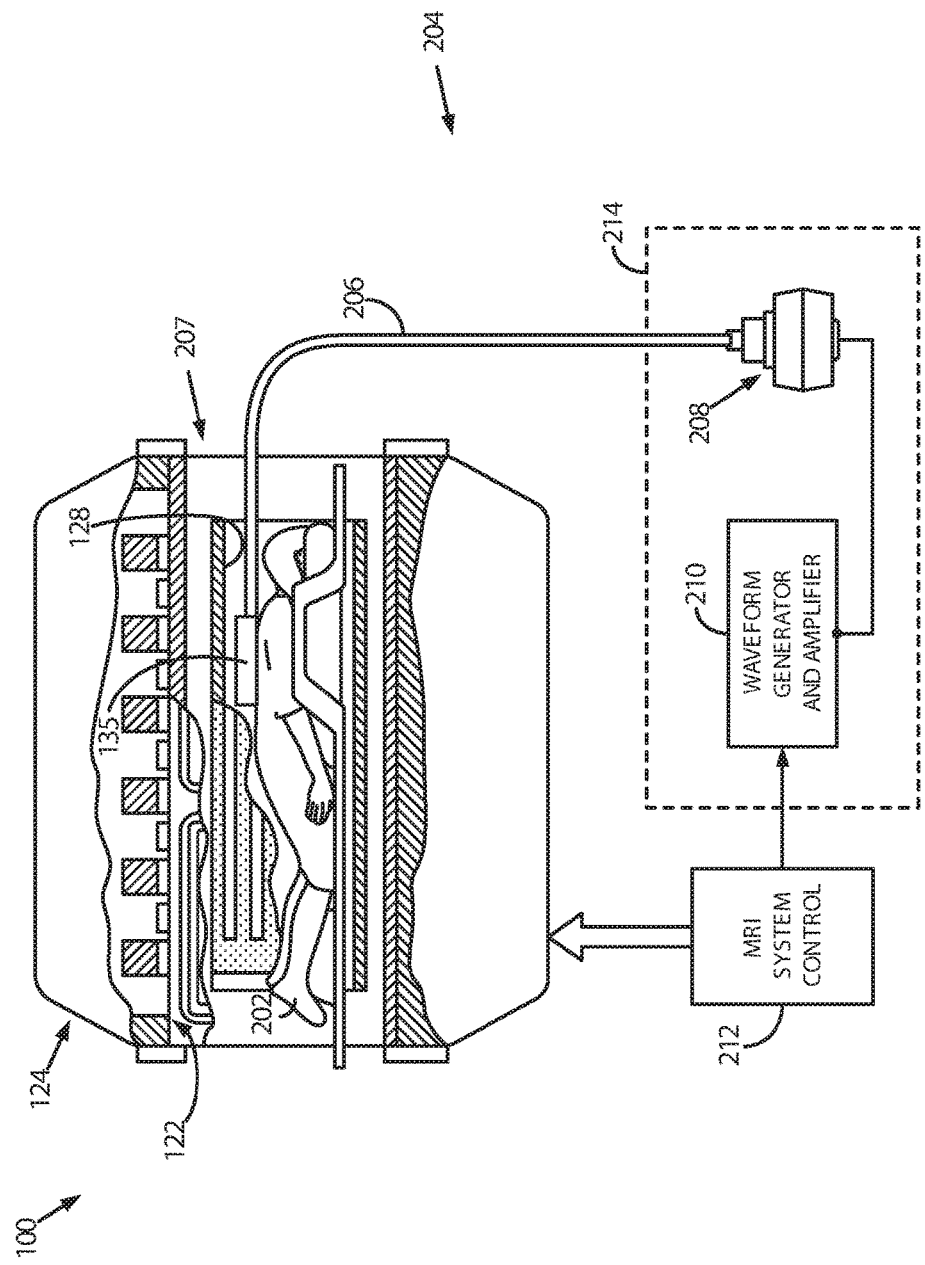
FIG. 2 shows a magnetic resonance elastography (MRE) driver of the MRI system of FIG. 1 according to one aspect of the present disclosure.

Referring now to FIG. 2, the MRE driver 135 of the present disclosure is illustrated as a passive driver system that may be placed on a subject 202 and energized to produce an oscillating, or vibratory, stress. Notably, however, the driver 135 may also be an active driver. The MRE driver 135 is part of a driver system 204. The driver 135 is positioned over a region-of-interest in the subject 202 and connected by means of a tube 206 to a remotely located active driver 208. The active driver 208 is remote from the bore 207 of the magnet assembly 124 in the sense that it is positioned away from the strong magnetic fields produced by the magnet assembly 124 where its operation is not impeded by those fields, and where its operation will not perturb the magnetic fields of the MRI system 100. The active driver 208 is electrically driven by a waveform generator and amplifier 210, which in turn is controlled by the pulse sequence server 110, which forms a part of the MRI system control 212. The MRI system control 212 directs the MRI system 100 to perform an MRE scan by driving the RF coil 128 and the gradient coils 122 in the magnet assembly 124 to perform a series of pulse sequences, while enabling the waveform generator 210 to apply an oscillatory stress to the subject 202 at the proper moment during each pulse sequence, as described in U.S. Pat. No. 5,592,085, which is herein incorporated by reference in its entirety. The active driver 208 and the waveform generator and amplifier 210 may be housed together in a manually portable unit, denoted by dashed line 214. Examples of driver systems are disclosed in U.S. Pat. Nos. 7,034,534 and 7,307,423; and in U.S. Patent Application Publications Nos. US2009/0299168 and US2010/0005892.

Using the above-described MRE driver system, the mechanical properties of tissue, such as soft tissue or organs, including the liver, can be measured using MRE by applying an oscillatory stress to the subject 202 and observing the resulting deformation. By measuring the resulting strain, mechanical properties of the tissue, such as Young's modulus, Poisson's ratio, stiffness, shear modulus, and bulk modulus can be calculated. By applying the stress in all three dimensions and measuring the resulting strain, the mechanical properties of the tissue can be defined.

Figure 3:
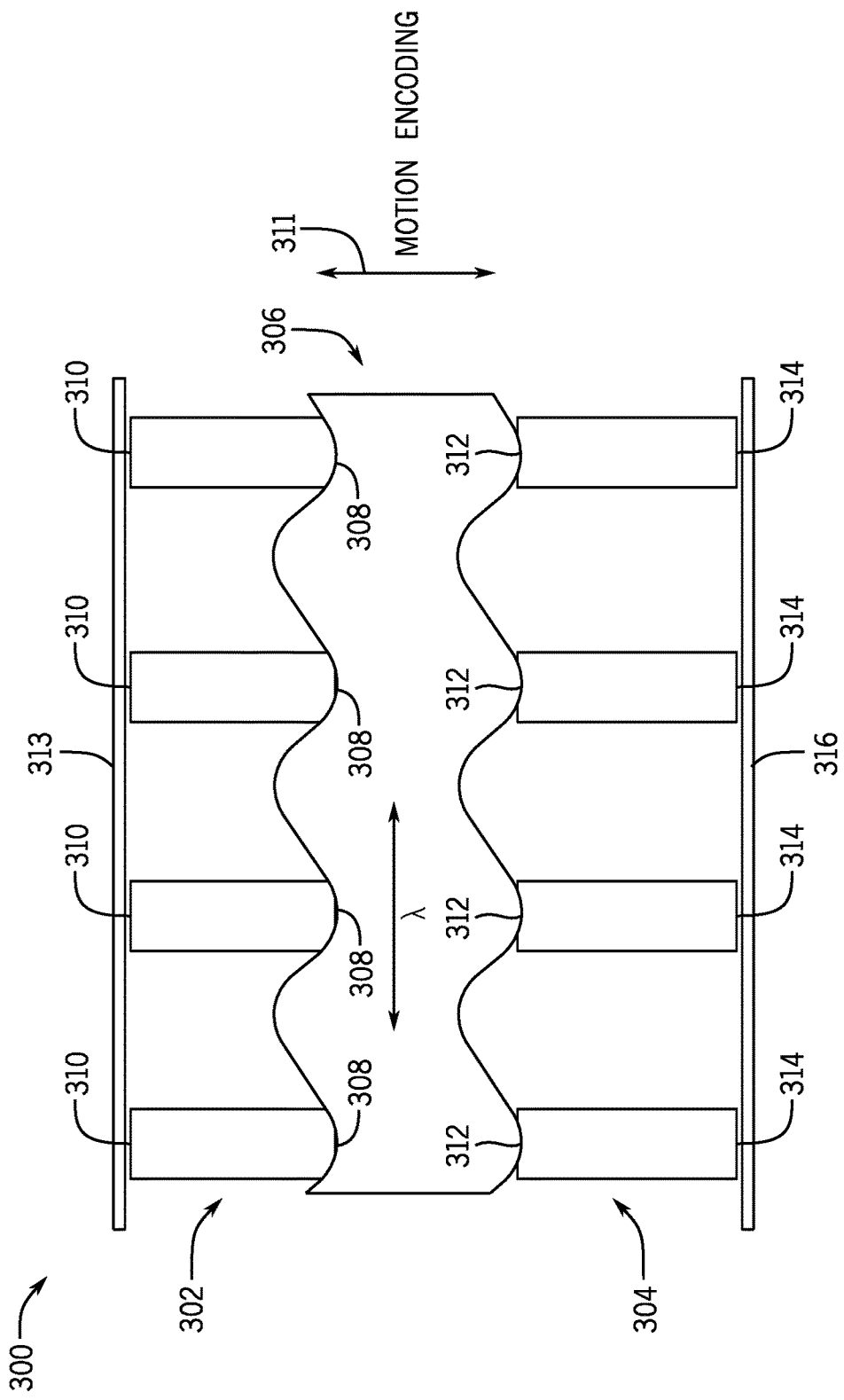
FIG. 3 shows a phantom according to one aspect of the present disclosure.

As described above, in order for MRE to accurately calculate the mechanical properties of the tissue, accurate calibrations are required to calculate the observed quantity (e.g., wavelength) to a mechanical property. FIG. 3 shows one non-limiting example of a phantom 300 for calibrating MRE image acquisition and mechanical property calculations. The phantom 300 includes a first plurality of supports 302, a second plurality of supports 304, and an MRI visible structure 306 arranged between the first plurality of supports 302 and the second plurality of supports 304. The use of term "MRI visible" herein refers to materials or components which yield MRI signal.

The first plurality of supports 302 each include a first end 308 that engage the MRI visible structure 306 and a second end 310. Each of the first plurality of supports 302 are arranged substantially parallel to a motion encoding, or out-of-plane, direction 311. The first plurality of supports 302 are spaced apart in a direction substantially perpendicular to the motion encoding direction 311 such that adjacent pairs of the first plurality of supports 302 each define a fixed distance therebetween. The second ends 310 of each of the first plurality of supports 302 are attached to a first coupling plate 313. The first coupling plate 313 couples each of the first plurality of supports 302 together such that the first plurality of supports 302 displace in unison. The first plurality of supports 302 are moveable (i.e., not fixed) in a direction generally parallel to the motion encoding direction 311. The first plurality of supports may be moveable in response to motion delivered to the phantom 300 in the motion encoding direction 311.

The second plurality of supports 304 each include a first end 312 that engage the MRI visible structure 306 on an opposing side of the MRI visible structure than the first plurality of supports 302, and a second end 314. Each of the second plurality of supports 304 are arranged substantially parallel to the motion encoding direction 311 and are directly opposing and/or parallel (i.e., generally aligned in the motion encoding direction 311) to the first plurality of supports 302. The second plurality of supports 304 are spaced apart in the direction substantially perpendicular to the motion encoding direction 311 such that adjacent pairs of the second plurality of supports 304 each have or define a fixed distance therebetween. The fixed distance between the adjacent pairs of the first plurality of supports 302 is substantially equal to the fixed distance between the adjacent pairs of the second plurality of supports 304.

The second ends 314 of each of the second plurality of supports 304 are attached to a second coupling plate 316. The second coupling plate 316 couples each of the second plurality of supports 304 together such that of the second plurality of supports 304 displace in unison. The illustrated second plurality of supports 304 are moveable in a direction substantially parallel to the motion encoding direction 311. The second plurality of supports 304 may be moveable in response to motion delivered to the phantom 300 in the motion encoding direction 311.

The MRI visible structure 306 is fabricated from or includes an MRI visible material capable of being displaced and flexing in response to motion delivered to the phantom 300. In one non-limiting example, the MRI visible structure 306 can be a container (e.g., a tube) filled with a MRI visible fluid (e.g., water). In another non-limiting example, the MRI visible structure 306 can be a sheet of MRI visible gel.

Regardless of the material and container selection, the MRI visible structure 306 is designed to be flexible, as will be described, when subjected to repeated displacing forces applied by the first plurality of supports 302 and the second plurality of supports 304. A thickness of the MRI visible structure 306 in the motion encoding direction 311 can be dimensioned to provide a reasonable signal-to-noise ratio (SNR) during an MRI scan, and may be varied from phantom to phantom for different applications.

In operation, motion can be delivered to the phantom 300 (e.g., via the MRE driver 135), which can move the entire phantom 300 including the first plurality of supports 302, the MRI visible structure 306, and the second plurality of supports 304 in the motion encoding direction 311. Since the first plurality of supports 302 are directly opposing the second plurality of supports 304, the motion of the areas of the MRI visible structure 302 pinched by the supports is constrained. The areas of the MRI visible structure 306 that are not pinched are free to displace with greater amplitude due to inertial effects, thus, when the phantom 300 is displaced in the motion encoding direction 311, the phantom 300 generates alternating areas of high amplitude and low amplitude (i.e., a wave-like pattern). A wavelength (λ) generated by the wave-like pattern generated by the phantom 300 can be controlled by the fixed distance between the adjacent pairs of the first plurality of supports 302 and the adjacent pairs of the second plurality of supports 304. Thus, the wavelength generated can be geometrically controlled by the phantom 300.

Figure 4:
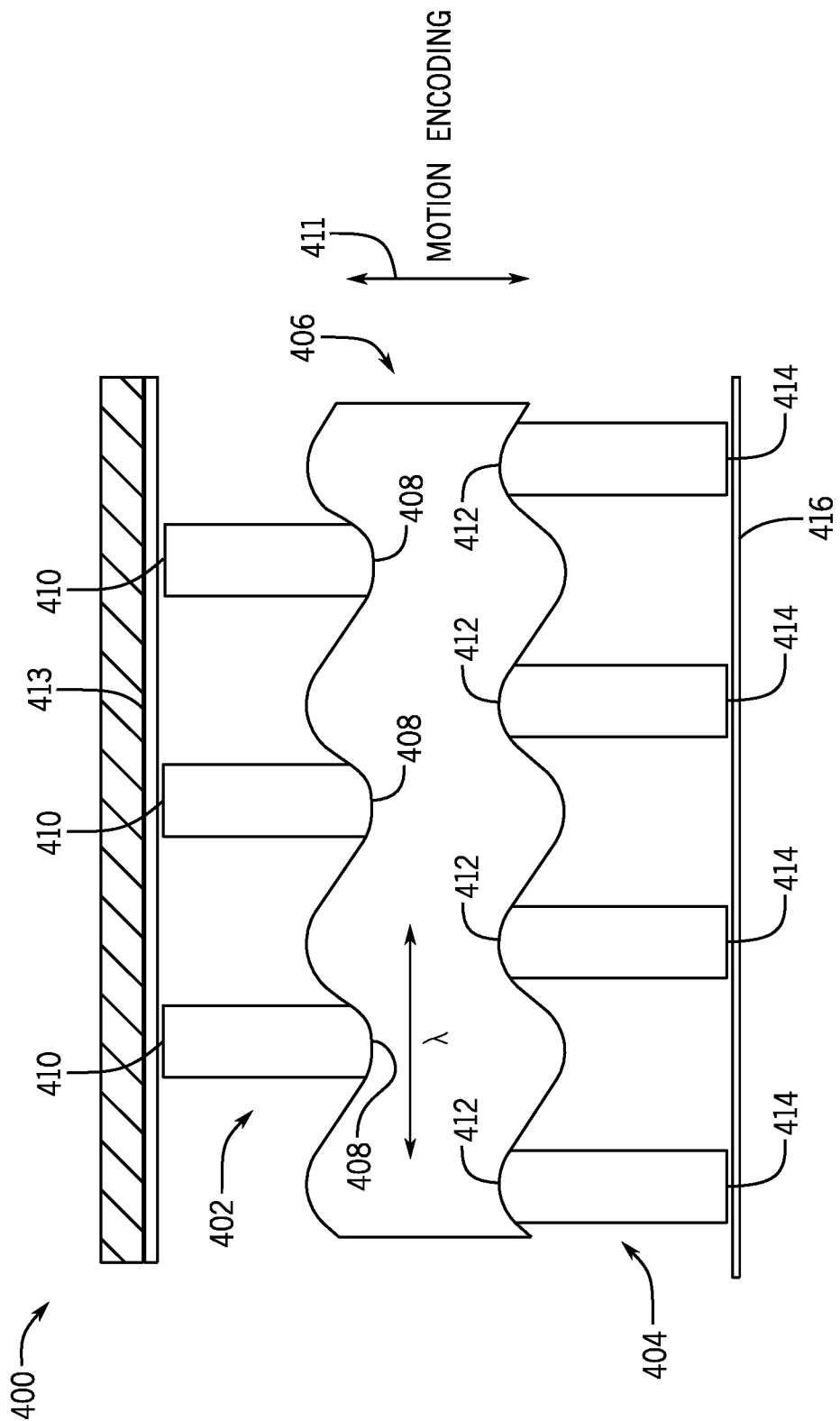
FIG. 4 shows another phantom according to another aspect of the present disclosure.

FIG. 4 shows another non-limiting example of a phantom 400 for calibrating MRE image acquisition and mechanical property calculations. The phantom 400 includes a first plurality of supports 402, a second plurality of supports 404, and an MRI visible structure 406 arranged between the first plurality of supports 402 and the second plurality of supports 404.

The first plurality of supports 402 each include a first end 408 that engage the MRI visible structure 406 and a second end 410. Each of the first plurality of supports 402 are arranged substantially parallel to a motion encoding, or out-of-plane, direction 411. The first plurality of supports 402 are spaced apart in a direction substantially perpendicular to the motion encoding direction 411 such that adjacent pairs of the first plurality of supports 402 define a fixed distance therebetween. The second ends 410 of each of the first plurality of supports 402 are attached to a first coupling plate 413. The first coupling plate 413 couples each of the first plurality of supports 402 together and can be fixed (e.g., by contacting the table of the MRI system 100, by a weigh of the first coupling plate 413, or by being connected to other fixed objects) thereby preventing the first plurality of supports 402 from displacing the in motion encoding direction 411.

The second plurality of supports 404 each include a first end 412 that engage the MRI visible structure 406 on an opposing side of the MRI visible structure than the first plurality of supports 402, and a second end 414. Each of the second plurality of supports 304 are arranged substantially parallel to the motion encoding direction 311 and are offset from the first plurality of supports 302 such that one of the first plurality of supports 302 are arranged between each adjacent pair of the second plurality of supports 304. In the illustrated non-limiting example, the second plurality of supports 404 can be arranged at a location approximately half-way between adjacent pairs of the first plurality of supports 402. The second plurality of supports 404 are spaced apart in the direction substantially perpendicular to the motion encoding direction 411 such that adjacent pairs of the second plurality of supports 404 have or define a fixed distance therebetween. The fixed distance between the adjacent pairs of the first plurality of supports 402 is substantially equal to the fixed distance between the adjacent pairs of the second plurality of supports 404.

The second ends 414 of each of the second plurality of supports 404 are attached to a second coupling plate 416. The second coupling plate 416 couples each of the second plurality of supports 404 together such that each of the second plurality of supports 404 displace in unison The illustrated second plurality of supports 404 are moveable in a direction substantially parallel to the motion encoding direction 411.

The MRI visible structure 406 can be similar to the MRI visible structure 306 of the phantom 300, described above. In operation, motion in the motion encoding direction 411 may be delivered to the second plurality of supports 404, which are moveable in the motion encoding direction 411 by the MRE driver 135. Motion of the second plurality of supports 404 can displace the MRI visible structure 406 at the locations where the first ends 412 contact the MRI visible structure 406. Simultaneously, the first plurality of supports 402, being generally fixed, prevents the MRI visible structure 406 from displacing in the motion encoding direction 411 at the locations where the first ends 408 contact the MRI visible structure 406. This can create alternating areas along the MRI visible structure 406 of low phase (areas in contact with the first plurality of supports 402) and high phase (areas in contact with the second plurality of supports 404) thereby generating a wave-like pattern. The wavelength (λ) defined by the wave-like pattern generated by the phantom 400 can be defined by the fixed distance between the adjacent pairs of the first plurality of supports 402. Thus, the wavelength generated can be geometrically controlled by the phantom 400.

It should be known that although the phantom 300 of FIG. 3 and the phantom 400 of FIG. 4 define different mechanical structure they both are configured to generate a wave-like pattern having a geometrically controlled wavelength via fixed and un-fixed areas of the MRI visible structures 306 and 406. One non-limiting example of the operation of the phantom 300 when calibrating an MRI system will be described with reference to FIGS. 1-3 and 5. It should be know that the exemplary advantages of the phantom 300 described herein, or otherwise apparent to one of skill in the art, may be applied to other phantoms designed using the techniques and properties described herein. Additionally, the operation of the phantom 300 described below also applies to the phantom 400.

Figure 5:
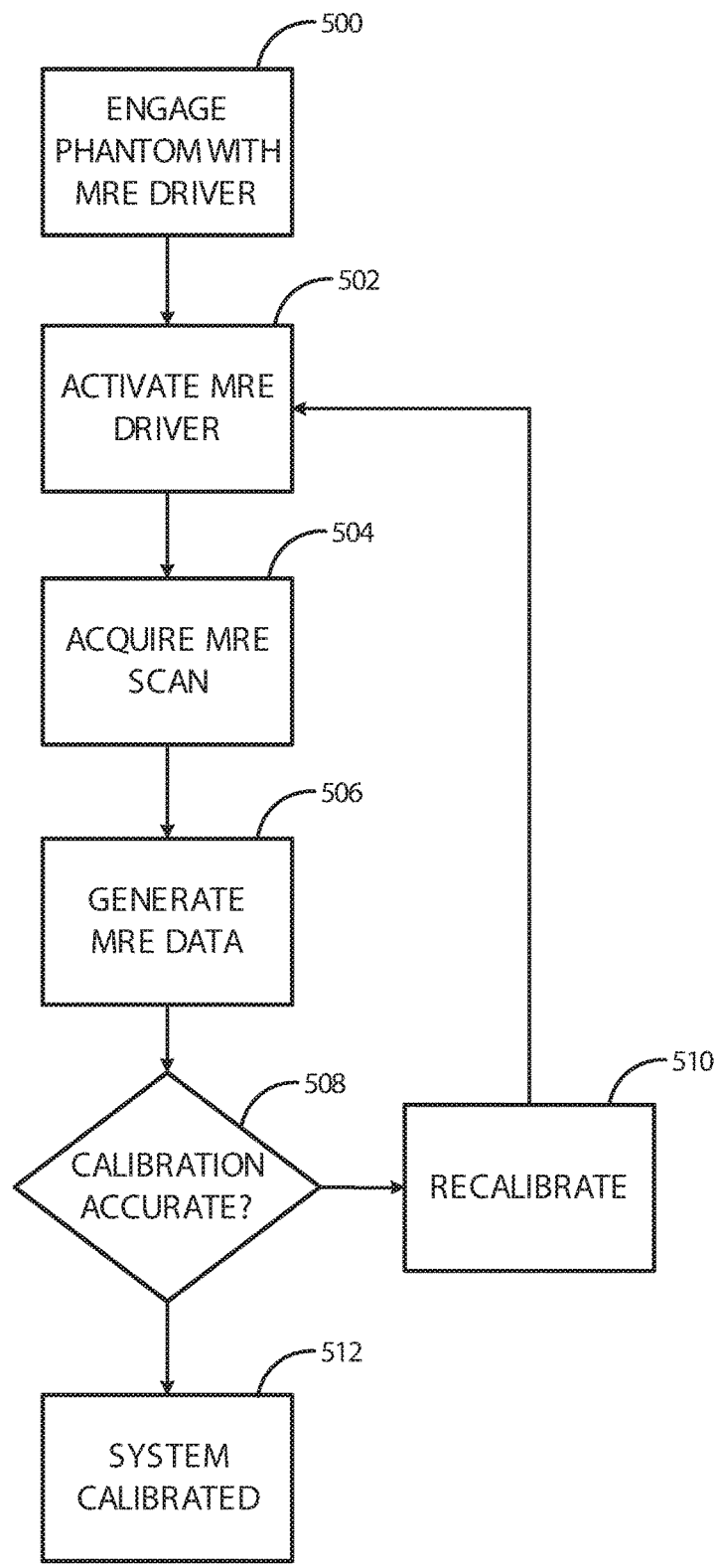
FIG. 5 shows the steps for calibrating MRE image acquisition and mechanical property calculation using the phantom of FIG. 3 or FIG. 4 according to one aspect of the present disclosure.

The phantom 300 can be used to calibrate MRE image acquisition and mechanical property calculation. FIG. 5 shows one non-limiting example of the steps for accomplishing this calibration using the phantom 300. As shown in FIG. 5, the calibration process begins by engaging, or securing, the phantom 300 to the MRE driver 135 at step 500. Once the phantom 300 is engaged to the MRE driver 135, the MRE driver is activated at step 502. Activating the MRE driver at step 502 vibrates the phantom 300, for example, at a frequency that would be used during a typical exam.

During vibration of the phantom 300 by the MRE driver 135 at step 502, the MRI visible structure 306 of the phantom 300 is pinched between the first plurality of supports 302 and the second plurality of supports 304 and free to displace in the motion encoding direction 311 in between the pinched areas. The first plurality of supports 302 and the second plurality of supports 304 limit an amplitude of vibration at the pinched locations along the MRI visible structure 306. The vibration of the MRI visible structure 306 in the motion encoding, or out-of-plane, direction 311 enables the MRI visible structure 306 to generate MRI phase. The locations along the MRI visible structure 306 pinched between the first plurality of supports 302 and the second plurality of supports 304 generate areas of low phase, and the locations between the pinched areas generate areas of high phase. Thus, the phantom 300 generates a smoothly varying phase pattern alternating between areas of high phase and areas of low phase. That is, the phantom 300 generates a wave-like pattern where the wavelength defined by the pattern is equal to the fixed distance between the adjacent pairs of the first plurality of supports 302 and the second plurality of supports. As described above, the MRI visible structure 306 yields MRI signal. Therefore, the wave-like pattern generated by the phantom 300 can be imaged by the MRI system.

Following activating the MRE driver 135 at step 502, a MRE scan is acquired of the phantom 300 at step 504. During the MRE scan of the phantom 300 at step 504, one or more MRE images are acquired of the phantom 300 using the MRI system 100. A wavelength within the one or more images of the phantom 300 should be equal to the distance between the adjacent pairs of the first plurality of supports 302 and the second plurality of supports. That is, the phantom 300 geometrically controls the wavelength generated by vibrating the phantom 300, which is then imaged during the MRE scan at step 504. It should be known that the thickness of the MRI visible structure 306 for whole-body MRI using clinical sequences can be greater than the thickness for small-animal scanners. However, the smaller thickness may enable greater flexibility of the MRI visible structure 306 resulting in a greater difference in motion amplitude between the low and high motion areas, and a clearer wave-pattern across the phantom.

The wave-like pattern with a known wavelength generated by the phantom 300 in the one or more images acquired during the MRE scan at step 504 is then used to generate MRE data at step 506. The MRE data generated at step 506 can include calculating using a known algorithm, or inversion, one or more mechanical properties. Once the MRE data is generated at step 506, the accuracy of the calibration of the MRI system 100 is determined at step 508. The accuracy of the calibration can be determined automatically at step 508 by the processor 108 or the data processing server 114. Alternatively or additionally, the accuracy of the calibration may be determined at step 508 by a user, or an imaging technician, of the MRI system 100 based on the calculated mechanical property at step 506. The mechanical property may be determined, for example, from an elastogram created from the MRE data.

In one non-limiting example, the value of the mechanical property determined at step 506 corresponds to the theoretical value calculated based on the known frequency and wavelength. Alternatively or additionally, it can be determined at step 508, based on the quality of the model fit during the calculation of step 506, if the MRE driver 135 provided sufficient wave amplitude to accurately calculate the mechanical property at step 506. If the calibration is not determined to be accurate at step 508, then the MRI system 100 and/or the algorithm, or inversion, used to calculate the mechanical property at step 506 may be recalibrated at step 510 and the steps 502-508 may be repeated until the calibration is accurate. If the calibration is determined to be accurate at step 508, then the MRI system 100 is properly calibrated at step 512 and capable of acquiring and calculating accurate MRE data.

It should be known that the geometry of the phantoms 300 and 400 (i.e., the distance between the adjacent pairs of the first plurality of supports 302 and 402 and the second plurality of supports 304 and 404) control the wavelength of the generated wave-like pattern Therefore, the phantoms 300 and 400 can be tunable (i.e., geometrically designed) to generate any wavelength, as desired, as long as the MRI visible material is able to flex at such wavelength with sufficient amplitude while maintaining structural integrity. Additionally, the properties and techniques disclosed herein may be used to calibrate the accuracy of the frequency generated by the MRE driver 135. For example, a phantom similar to the phantom 300 can be constructed that includes a plurality of MRI visible structures 306 each with different mechanical properties (e.g., dimensions, masses, tensions, etc.), and thus different resonant frequencies. The amplitudes of vibration for each of the plurality of MRI visible structures 306 can then be compared to determine the accuracy of the frequency generated by the MRE driver. Further, multiple scans of the phantom 300 may be acquired to simulate a propagating wave by either mechanically moving the phantom 300 or shifting the field of view of the MRI system 100. However, since the wavelength of the generated wave-like pattern is geometrically controlled, and fixed, the phantom 300 yields the same calculated mechanical property for both a standing wave and a simulated propagating wave. The phantoms 300 or 400, or any other phantoms designed using similar properties and techniques, enable the calibration of MRE image acquisition and mechanical property calculation, which is not subject to unknown mechanical properties of the MRI visible structure 306 by geometrically controlling a wavelength of a generated wave-like pattern.

In one non-limiting example, the above-described phantom can be machined with precisely controlled geometry, yielding a well-controlled and known wavelength. It is not affected by moderate changes in gel properties. Thus, the phantom of the present disclosure resolves the issues of existing gels, which are that the true stiffness is unknown, manufacturing differences cause perceivable differences in stiffness, and stiffness changes over time. As a result, the above-described phantom can be useful in multi-site and longitudinal studies.

Thus, while the invention has been described above in connection with particular embodiments and examples, the invention is not necessarily so limited, and numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A phantom for a magnetic resonance elastography (MRE) system, the phantom comprising:
    an MRI visible structure configured to be flexible when subjected to displacing forces;
    a first plurality of supports each engaging one side of the MRI visible structure, wherein the first plurality of supports are spaced apart such that adjacent pairs of the first plurality of supports define a first distance therebetween;
    a second plurality of supports each engaging another opposing side of the MRI visible structure, wherein the second plurality of supports are spaced apart such that adjacent pairs of the second plurality of supports define the first distance therebetween; and wherein repeated motion of the second plurality of supports in a displacement direction causes displacement of the MRI visible structure to create a wave-like pattern in the MRI visible structure.

2. The phantom of claim 1, wherein the first plurality of supports are arranged substantially parallel to the second plurality of supports.

3. The phantom of claim 1, wherein the first plurality of supports are directly opposing the second plurality of supports.

4. The phantom of claim 3, wherein the first plurality of supports and the second plurality of supports are moveable in the displacement direction.

5. The phantom of claim 3, wherein the first plurality of supports and the second plurality of supports reduce an amplitude of displacement of the MRI visible structure at locations where the first plurality of supports and the second plurality of supports engage the MRI visible structure.

6. The phantom of claim 1, wherein the first plurality of supports are offset from the second plurality of supports in a direction perpendicular to the displacement direction.

7. The phantom of claim 6, wherein the first plurality of supports are generally fixed thereby preventing the first plurality of supports from displacing in the displacement direction.

8. The phantom of claim 6, wherein the second plurality of supports are moveable in the displacement directions.

9. The phantom of claim 6, wherein one of the first plurality of supports are arranged at a location approximately half way in between each adjacent pair of the second plurality of supports.

10. The phantom of claim 6, wherein the first plurality of supports inhibit discrete locations along the MRI visible structure from displacing in the displacement direction.

11. The phantom of claim 1, wherein the wave-like pattern forms an appearance of a standing wave or a propagating wave in MR images acquired of the MRI visible structure.

12. The phantom of claim 1, wherein the MRI visible structure comprises a flexible material that yields MRI signal.

13. The phantom of claim 1, wherein the MRI visible structure comprises a sheet of MRI-visible gel.

14. The phantom of claim 1, wherein the MRI visible structure comprises a flexible container filled with an MRI visible fluid.

15. The phantom of claim 14, wherein the MRI visible fluid is water.

16. A method for calibrating a magnetic resonance imaging (MRI) system used to acquire magnetic resonance elastography (MRE) data with a phantom, the phantom including an MRI visible structure, the method comprising:

engaging the phantom with an MRE driver configured to impart an oscillating motion to the phantom by displacing flexible portions of the phantom to create alternating areas of high phase and low phase forming a wave-like pattern defining a wavelength geometrically controlled by the phantom;

acquiring, with the MRI system, an MRE data from the phantom while using the MRE driver to create the alternating areas of high phase and low phase in a wave-like pattern; and analyzing the MRE data to determine a calibration state of the MRI system.

17. The method of claim 16, wherein analyzing MRE data comprises calculating one or more mechanical properties of the phantom from the MRE data and comparing the one or more mechanical properties to expected mechanical properties.

18. The method of claim 17, further comprising comparing a frequency of the one or more calculated mechanical properties to a frequency used by the MRE driver to create the oscillating motion.

19. The method of claim 16, wherein analyzing the MRE data comprises analyzing an amplitude of the wave-like pattern.

20. A phantom for a magnetic resonance elastography (MRE) system, the phantom comprising:

an MRI visible structure forming an elongated, flexible body;

a first plurality of supports each engaging one side of the MRI visible structure and spaced apart such that adjacent pairs of the first plurality of supports define a first distance therebetween;

a second plurality of supports each engaging another opposing side of the MRI visible structure and spaced apart such that adjacent pairs of the second plurality of supports define the first distance therebetween; and a driver configured to repeatedly move the second plurality of supports to cause displacement of the MRI visible structure to create a wave-like pattern in the MRI visible structure.

* * * * *

UNITED STATES PATENT AND TRADEMARK OFFICE
CERTIFICATE OF CORRECTION

| | |
|---|---|
| PATENT NO. | : 10,132,905 B2 |
| APPLICATION NO. | : 15/399479 |
| DATED | : November 20, 2018 |
| INVENTOR(S) | : Dzyubak et al. |

Page 1 of 1

It is certified that error appears in the above-identified patent and that said Letters Patent is hereby corrected as shown below:

In the Specification

Column 5, Line 19, "114 re" should be --114 are--.

Column 7, Line 23, "(A)" should be --($\lambda$)--.

Signed and Sealed this
Twenty-ninth Day of January, 2019

Andrei Iancu
*Director of the United States Patent and Trademark Office*